US008541213B2

(12) United States Patent
Yoneda et al.

(10) Patent No.: US 8,541,213 B2
(45) Date of Patent: Sep. 24, 2013

(54) RECOMBINANT YEAST AND BRANCHED ALCOHOL PRODUCTION METHOD USING RECOMBINANT YEAST

(75) Inventors: Satoshi Yoneda, Toyota (JP); Masayoshi Muramatsu, Miyoshi (JP); Shusei Obata, Nagoya (JP); Ai Inoue, Owariasahi (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 0 days.

(21) Appl. No.: 13/619,386

(22) Filed: Sep. 14, 2012

(65) Prior Publication Data

US 2013/0011892 A1 Jan. 10, 2013

Related U.S. Application Data

(62) Division of application No. 12/794,393, filed on Jun. 4, 2010, now abandoned.

(30) Foreign Application Priority Data

Jun. 4, 2009 (JP) .................................. 2009-134937

(51) Int. Cl.
*C12P 7/04* (2006.01)
(52) U.S. Cl.
USPC ......................................................... 435/157
(58) Field of Classification Search
None
See application file for complete search history.

(56) References Cited

U.S. PATENT DOCUMENTS

| 2004/0029239 A1 | 2/2004 | Ohto et al. |
| 2008/0213847 A1 | 9/2008 | Ohto et al. |

FOREIGN PATENT DOCUMENTS

| JP | 2003-180371 B2 | 7/2003 |
| JP | 3838033 B2 | 10/2006 |
| JP | 3894119 B2 | 3/2007 |
| WO | 2007/041269 A2 | 4/2007 |
| WO | 2007/139925 A2 | 12/2007 |
| WO | 2008/052991 A2 | 5/2008 |

OTHER PUBLICATIONS

Nieto A et al.: "Stable High-Copy-Number Integration of *Aspergillus orysae* a-Amylase cDNA in an Industrial Baker's Yeast Strain", (1999) Biotechno. Prog., 15 (3), 459-66.
Shota Atsumi, et al., "Non-Fermentative Pathways for Synthesis of Branched-Chain High Alcohols as Biofeuls", Nature, Jan. 3, 2008, pp. 86-89, vol. 451, Nature Publishing Group, Los Angeles/CA, USA.
Sydnor T. Withers, et al., "Identification of Isopentenol Biosynthetic Genes from *Bacillus subtilis* by a Screening Method Based on Isoprenoid Precursor Toxicity", Applied and Environmental Microbiology, Oct. 2007, pp. 6277-6283, vol. 73, No. 19.
Hisao Ito, et al., "Transformation of Intact Yeast Cells Treated with Alkali Cations", Journal of Bateriology, Jan. 1983, pp. 163-168, vol. 153, No. 1.
Claire L. Pearson, et al., "Analysis of the Function of a Putative 2, 3-Diphosphoglyceric Acid-Dependent Phosphoglycerate Mutase from *Bacillus subtilis*", Journal of Bacteriology, Jul. 2000, pp. 4121-4123, vol. 182, No. 14.
Shunji Takahashi, et al., "Purification, Characterization, and Closning of a Eubacterial 3-Hydroxy-3-Methylglutaryl Coenzyme A Reductase, a Key Enzyme Involved in Biosynthesis of Terpenoids", Journal of Bcateriology, Feb. 1999, pp. 1256-1263, vol. 181, No. 4, 1999.
F. Schirmaier, et al., "High-Efficiency Transformation of Yeast by Electroporation", Method in Enzymology, 1984, pp. 182-187, vol. 194.
Albert Hinnen, et al., "Transformation of Yeast", Proc. Natl. Acad. Sci., Apr. 1978, pp. 1929-1933, vol. 75, No. 4.
Schmidt, et al., "Recombinant Expression Systems in the Pharmaceutical Industry", Appl. Microbiol. Biotechnol. (2004) 65:363-372.

*Primary Examiner* — Tekchand Saidha
*Assistant Examiner* — Md. Younus Meah
(74) *Attorney, Agent, or Firm* — Sughrue Mion, PLLC (57) ABSTRACT

This invention provides a recombinant yeast that can produce branched alcohol appropriate for automotive fuel and the like and a branched alcohol production method whereby branched alcohol can be produced at low cost with the use of the recombinant yeast. A recombinant yeast in which a hydroxymethyl glutaryl-CoA reductase gene has been expressed to a high degree and the ADP-ribose pyrophosphatase gene and/or the yhfR gene are introduced so as to be expressed therein is provided.

7 Claims, 3 Drawing Sheets

Fig. 1 nudF gene
GGGCCGCGGACTAGTGCCGCCACCatgaaatcattagaagaaaaaacaattgccaaagaacagattttttc
tggtaaagtcattgatctttatgtcgaggatgtagagctgccaaacggcaaagccagtaaacgtgaaattgtgaaacaccctg
gagctgtagcggtactagccgtcacagatgaagggaaaatcatcatggtcaaacaattccgtaagccgcttgagagaacgat
cgttgaaattccggccggtaagcttgaaaaaggtgaggagccggagtatacggcacttagagaacttgaagaggaaaccgg
ttatacagcaaaaaaactgacaaaaataactgcgttttatacatcacccggatttgcagatgaaatcgttcacgtttttcttgct
gaggagctttctgtgcttgaagaaaaagagagcttgatgaggacgagtttgttgaagtgatggaggtgacgcttgaagatg
cgctaaagctggttgaatctagagaagtatatgatgctaaaacagcctacgcgattcagtatcttcagctgaaagaagcgctc
caagcacaaaaatgaGATATCGTCGACGGGG (SEQ ID NO: 26)

yhfR gene
GGGTCTAGAACTAGTGCCGCCACCatgacagccgtttgtttagtaagacatggagaaaccgattggaacctg
cagcaaaaatgccaaggcaaaaccgatatcccgctaaacgcaacaggtgaaagacaagcaagagaaaccggagaatatgt
aaaggacttttcttgggatattattgtgacgagcccgctgaaaagagcgaaaagaaccgcggaaattattaatgaatatctgc
atcttccgatagtcgagatggatgattttaaggaaagagattacggcgacgcggagggcatgccgctggaggaaagaacaa
agcgctatccagataacatctatccgaatatggaaaccttagaagaattgactgacaggctgatgggcggtttggcaaaagtg
aatcaggcgtatccaaacaagaaggtgctgatcgtggcgcacggtgcggcaattcacgccctgctgacagaaatatccggcgg
tgacccggagcttcaaagcacccgtttggtcaacgcctgcttgagcaacattgaatttgcagaagaaaaatggagaataaaa
gactataatatcaacagccacttatccggctttatcaaataaGAATTCGTCGACGGGG (SEQ ID NO: 27)

RECOMBINANT YEAST AND BRANCHED ALCOHOL PRODUCTION METHOD USING RECOMBINANT YEAST

CROSS REFERENCE TO RELATED APPLICATION(S)

This application is a divisional of U.S. Ser. No. 12/794,393, filed on Jun. 4, 2010, now pending, which claims priority to Japanese patent application 2009-134937, filed on Jun. 4, 2009. The disclosure of each of the prior applications is considered part of and is incorporated herein by reference in its entirety.

BACKGROUND OF THE INVENTION

1. Field of the Invention

The present invention relates to a recombinant yeast having a predetermined gene introduced therein and a branched alcohol production method using the recombinant yeast.

2. Background Art

In recent years, the following problems have been arising regarding ethanol used as automotive fuel: the energy density thereof is low and the characteristics thereof significantly differ from those of conventional petroleum fuel. Therefore, studies have been conducted to produce butanol or the like, which is an alcohol with an extended carbon chain length serving as fuel characteristically closer to petroleum fuel, by a fermentative production method with the use of *Escherichia coli* and yeast (see WO 2007/041269 and WO 2008/052991). In addition, since a gasoline fuel with the high octane number of such a straight-chain alcohol is preferably used, fuels comprising 2-methyl-1-butanol, 3-methyl-1-butanol, and the like have been also studied (*Nature* 451, 86-89, (2008)).

Meanwhile, it has been reported that 2-methyl-1-butenol can be synthesized by causing the expression of the nudF gene or yhfR gene of *Bacillus subtilis* in *Escherichia coli*. In addition, it has been revealed that expression products of the nudF gene and the yhfR gene convert dimethylallyl-diphosphate or isopentenyl diphosphate into 2-methyl-3-butene-1-ol (*Appl. Environ. Microbiol.* 73, 6277-83 (2007)). Further, it has been reported that 3-methyl-2-butene-1-ol and 3-methyl-3-butene-1-ol can be synthesized by causing the expression of the above genes in *Escherichia coli* in a similar manner (WO 2007/139925).

SUMMARY OF THE INVENTION

It is generally thought that the amino acid synthesis pathway is used for synthesizing a branched alcohol with a certain chain length such as 2-methyl-1-butanol or 3-methyl-1-butanol, which is appropriate for automotive fuel and the like. However, regarding branched alcohol production with the use of the amino acid synthesis pathway, the supply shortage of amino acids necessary for microorganism growth is a matter of concern. There are still problems for mass-production of branched alcohol, which is a product of interest. In addition, a method involving the use of the nudF gene or the yhfR gene of *Bacillus subtilis* is advantageous because it does not involve the use of the amino acid synthesis pathway. However, the resulting branched alcohol has unsaturated bonds, and therefore the oxidative stability is poor when such alcohol is used as fuel, which is problematic. In addition, it is possible to reduce unsaturated bonds with a step of adding hydrogen to synthesized branched alcohol, for example. However, such step is cost-consuming, which is also problematic.

In view of the above circumstances, it is an object of the present invention to provide a recombinant yeast that can produce branched alcohol appropriate for automotive fuel and the like. It is another object of the present invention to provide a branched alcohol production method whereby branched alcohol can be produced at low cost with the use of the recombinant yeast.

As a result of intensive studies in order to achieve the above object, the present inventors have found that a desired branched alcohol can be produced by causing the expression of the ADP-ribose pyrophosphatase gene and/or the yhfR gene in a yeast in which a gene encoding hydroxymethyl glutaryl-CoA (HMG-CoA) reductase has been expressed to a high degree. This has led to the completion of the present invention.

Specifically, the recombinant yeast of the present invention is a recombinant yeast in which a hydroxymethyl glutaryl-CoA reductase gene has been expressed to a high degree, and the ADP-ribose pyrophosphatase gene and/or the yhfR gene are introduced so as to be expressed therein. For the recombinant yeast of the present invention, the nudF gene of *Bacillus subtilis* is preferably used as the ADP-ribose pyrophosphatase gene. In addition, for the recombinant yeast of the present invention, the yhfR gene of *Bacillus subtilis* is preferably used as the above yhfR gene. Further, for the recombinant yeast of the present invention, the HMG1 gene of *Saccharomyces cerevisiae* is preferably used as the above hydroxymethyl glutaryl-CoA reductase gene.

In addition, for the recombinant yeast of the present invention, a host is preferably a yeast having a mevalonic acid pathway, more preferably a yeast of the genus *Saccharomyces*, and most preferably *Saccharomyces cerevisiae*.

By culturing the above recombinant yeast of the present invention, branched alcohols, and particularly saturated branched alcohols such as 2-methyl-1-butanol and 3-methyl-1-butanol, can be collected from the medium.

Effects of the Invention

The recombinant yeast of the present invention has an excellent feature of producing a desired branched alcohol that can be used as an automotive fuel and a resin material. With the use of the recombinant yeast of the present invention, the above branched alcohol can be produced at low cost.

DESCRIPTION OF THE PREFERRED EMBODIMENTS

Hereinafter, the recombinant yeast of the present invention and the branched alcohol production method using the recombinant yeast are described in detail.

The recombinant yeast of the present invention is obtained by introducing the ADP-ribose pyrophosphatase gene and/or the yhfR gene into a yeast in which the hydroxymethyl glutaryl-CoA (HMG-CoA) reductase gene has been expressed to a high degree. In other words, the recombinant yeast of the present invention is a yeast that has been modified in a manner such that the HMG-CoA gene expression level and the expression level(s) of the ADP-ribose pyrophosphatase gene and/or the yhfR gene become greater than those of a wild-type yeast.

ADP-Ribose Pyrophosphatase Gene

The ADP-ribose pyrophosphatase gene of the present invention is not particularly limited, and therefore a gene from any organism can be used. Specifically, any gene can be used as the ADP-ribose pyrophosphatase gene, regardless of its origin, as long as it is a gene encoding ADP-ribose pyrophosphatase specified with the enzyme commission number EC 3.6.1.13. An example of the ADP-ribose pyrophosphatase gene is the nudF gene (SEQ ID NO: 1) of *Bacillus subtilis*. SEQ ID NO: 2 represents the amino acid sequence of a protein encoded by the nudF gene of *Bacillus subtilis*.

The "ADP-ribose pyrophosphatase gene" of the present invention includes a gene homologous to a *Bacillus subtilis*-derived gene. In general, a homologous gene can refer to a gene that has evolved and branched from a common ancestor gene. Such genes include a homologous gene (ortholog) for two different species and a homologous gene (paralog) generated as a result of overlapping branching in a single species.

In addition, the ADP-ribose pyrophosphatase gene of the present invention is not limited to *Bacillus subtilis*-derived genes. The ADP-ribose pyrophosphatase gene includes a gene encoding a protein having an amino acid sequence with a similarity of, for example, 70% or more, preferably 80% or more, more preferably 90% or more, and most preferably 95% or more to the amino acid sequence represented by SEQ ID NO: 2 and having ADP-ribose pyrophosphatase activity. Herein, such a similarity value refers to a value determined as a default setting with the use of a computer program (the BLAST (Basic Local Alignment Search Tool) program) and a database containing gene sequence information.

Examples of the gene encoding a protein having a high similarity to the amino acid sequence (SEQ ID NO: 2) of *Bacillus subtilis*-derived ADP-ribose pyrophosphatase include the gene specified as "GK2320" of *Geobacillus kaustophilus* HTA426, the gene specified as "OB1851" of *Oceanobacillus iheyensis* HTE831, the gene specified as "BSPH 1706" of *Lysinibacillus sphaericus* C3-41, the gene specified as "LIN2079" of *Listeria innocua* Clip11262, the gene specified as "AMET_2521" of *Alkaliphilus metalliredigens* QYMF, the gene specified as "EF2696" of *Alkaliphilus metalliredigens* QYMF, the gene specified as "TTE1310" of *Thermoanaerobacter tengcongensis* MB4T, the gene specified as "SA1330" of *Staphylococcus aureus* N315, the gene specified as "DRED_1901" of *Desulfotomaculum reducens* MI-1, and the gene specified as "PTH_1329" of *Pelotomaculum thermopropionicum* S1. In addition, identifiers that allow the identification of such genes are registered in the "Entry" section in the KEGG database.

Further, it is also possible to use a gene from an organism with unknown genomic information as the ADP-ribose pyrophosphatase gene of the present invention. For instance, the genome is extracted from an organism of interest or the cDNA library of an organism of interest is constructed, followed by isolation of a genomic region or cDNA that hybridizes to at least a portion of a polynucleotide complementary to the nucleotide sequence represented by SEQ ID NO: 1 under stringent conditions. Thus, the ADP-ribose pyrophosphatase gene of the organism can be identified/isolated. The term "stringent conditions" used herein refers to conditions that cause formation of a so-called specific hybrid but not a nonspecific hybrid. For example, such conditions include hybridization at 45° C. with 6×SSC (sodium chloride/sodium citrate) and the subsequent washing at 50° C. to 65° C. with 0.2 to 1×SSC and 0.1% SDS. Alternatively, the conditions include hybridization at 65° C. to 70° C. with 1×SSC and the subsequent washing at 65° C. to 70° C. with 0.3×SSC. Hybridization can be performed by a conventionally known method such as the method described in J. Sambrook et al., Molecular Cloning, A Laboratory Manual, 2nd Ed., Cold Spring Harbor Laboratory (1989).

Furthermore, the ADP-ribose pyrophosphatase gene of the present invention is not particularly limited to wild-type genes from a variety of organisms as described above. A mutant ADP-ribose pyrophosphatase gene that has been artificially mutated may also be used. An example of a mutant ADP-ribose pyrophosphatase gene is a gene encoding a protein having an amino acid sequence derived from the amino acid sequence encoded by the wild-type ADP-ribose pyrophosphatase gene by deletion, substitution, addition, or insertion of 1 or more amino acid(s) and having ADP-ribose pyrophosphatase activity. An example of such gene that can be used is a mutant ADP-ribose pyrophosphatase gene encoding a protein having an amino acid sequence derived from the amino acid sequence (SEQ ID NO: 2) of *Bacillus subtilis*-derived ADP-ribose pyrophosphatase by deletion, substitution, addition, or insertion of, for example, 1 to 20 amino acids, preferably 1 to 10 amino acids, more preferably 1 to 7 amino acids, further preferably 1 to 5 amino acids, and particularly preferably 1 to 3 amino acids and having ADP-ribose pyrophosphatase activity.

Moreover, deletion, substitution, or addition of amino acids can be carried out by modifying the nucleotide sequence encoding the above wild-type ADP-ribose pyrophosphatase gene by a technique known in the art. Mutagenesis of the nucleotide sequence can be carried out by a known technique such as the Kunkel method, the gapped duplex method, or a method similar to either thereof with the use of, for example, a mutagenesis kit (e.g., Mutant-K and Mutant-G (product names; TAKARA Bio Inc.)) for a site-specific mutagenesis method, an LA PCR in vitro Mutagenesis series kit (product name, TAKARA Bio Inc.), or the like. In addition, as a mutagenesis method, a method using agents that cause chemical mutation such as EMS (ethyl methanesulfonate), 5-bromouracil, 2-aminopurine, hydroxylamine, N-methyl-N'-nitro-N-nitroso guanidine, and other carcinogenic compounds, or a method involving treatment with radioactive rays such as X-rays, α-rays, β-rays, and γ-rays, an ion beam, or ultraviolet rays may be used.

yhfR Gene

The yhfR gene of the present invention includes a *Bacillus subtilis*-derived yhfR gene, a gene homologous to the yhfR gene from an organism other than *Bacillus subtilis*, and a gene encoding a protein having a high similarity to the protein encoded by the yhfR gene of *Bacillus subtilis*. SEQ ID NO: 3 represents the yhfR gene from *Bacillus subtilis*. SEQ ID NO: 4 represents the amino acid sequence of a protein encoded by the yhfR gene. The yhfR gene from *Bacillus subtilis* has been known as a gene encoding a protein highly homologous to phosphoglycerate mutase, although the functions thereof have not been accurately identified (Pearson C. L. et al., *J Bacteriol* (2000) 182:4121-4123). Therefore, the yhfR gene of the present invention can also be referred to as a gene encoding phosphoglycerate mutase.

In general, a gene homologous to the yhfR gene found in an organism other than *Bacillus subtilis* can be referred to as a gene that has evolved and branched from a common ancestor gene. Such genes include a homologous gene (ortholog) for two different species and a homologous gene (paralog) generated as a result of overlapping branching in a single species.

Genes encoding proteins having a high similarity to the protein encoded by the yhfR gene of *Bacillus subtilis* include a gene encoding a protein having an amino acid sequence with a similarity of, for example, 70% or more, preferably 80% or more, more preferably 90% or more, and most preferably 95% or more to the amino acid sequence represented by SEQ ID NO: 4. Herein, such a similarity value refers to a value determined as a default setting with the use of a computer program (the BLAST (Basic Local Alignment Search Tool) program) and a database containing gene sequence information.

Examples of a gene encoding a protein having a sequence with a high similarity to the amino acid sequence (SEQ ID NO: 4) of the protein encoded by a *Bacillus subtilis*-derived yhfR gene include the gene specified as "OB0337" of *Oceanobacillus iheyensis* HTE831, the gene specified as "EXIG_2819" of *Exiguobacterium sibiricum* 255-15, the gene specified as "KRAD_3374" of *Kineococcus radiotolerans* SRS30216, the gene specified as "PTH_1315" of *Pelotomaculum thermopropionicum* SI, the gene specified as "ARTH_0069" of *Arthrobacter* sp. FB24, the gene specified as "DARO_0602" of *Dechloromonas aromatics*, the gene specified as "LINO_293" of *Listeria innocua* Clip11262, the gene specified as "STH2126" of *Symbiobacterium thermophilum* IAM 14863, the gene specified as "KPN_04850" of *Klebsiella pneumoniae* ATCC 700721, and the gene specified as "EBA1038" of *Azoarcus* sp. EbN1. In addition, identifiers capable of identifying such genes are registered in the "Entry" section in the KEGG database.

Further, it is also possible to use a gene from an organism with unknown genomic information as the yhfR gene of the present invention. The technique described in the "ADP-ribose pyrophosphatase gene" section can be applied to the yhfR gene from an organism with unknown genomic information.

Furthermore, the yhfR gene of the present invention is not limited to wild-type genes from a variety of organisms as described above. Therefore, a mutant yhfR gene that has been artificially mutated can also be used. For example, an example of a mutant yhfR gene is a gene encoding a protein having an amino acid sequence derived from the amino acid sequence encoded by the wild-type yhfR gene by deletion, substitution, addition, or insertion of 1 or more amino acid(s). As an example of such gene, it is possible to use a mutant yhfR gene encoding a protein having an amino acid sequence derived from the amino acid sequence (SEQ ID NO: 4) of the *Bacillus subtilis*-derived yhfR gene by deletion, substitution, addition, or insertion of, for example, 1 to 20 amino acids, preferably 1 to 10 amino acids, more preferably 1 to 7 amino acids, further preferably 1 to 5 amino acids, and particularly preferably 1 to 3 amino acids.

Further, deletion, substitution, or addition of amino acids can be carried out by a technique described in the aforementioned "ADP-ribose pyrophosphatase gene" section.

HMG-CoA Reductase Gene

The HMG-CoA reductase gene of the present invention, which has been expressed to a high degree in a host, is not particularly limited. Therefore, a gene from any organism can be used. Specifically, regardless of the origin, any gene can be used as the HMG-CoA reductase gene as long as it is a gene encoding an enzyme specified as EC 1.1.1.34. The HMG-CoA reductase is an enzyme involved in the mevalonic acid pathway in which dimethylallyl diphosphate is biosynthesized from acetyl-CoA, such enzyme reducing 3-hydroxy-3-methyl glutaryl-CoA to result in mevalonic acid. The mevalonic acid pathway is known as a metabolic pathway found in substantially all organisms. A gene from any organism, which has the mevalonic acid pathway, can be used as the HMG-CoA reductase gene of the present invention.

For instance, examples of the HMG-CoA reductase gene that can be used include the HMG1 gene and the HMG2 gene from *Saccharomyces cerevisiae*, the HMG-CoA reductase gene from *Streptomyces* sp. CL190 (S Takahashi et al., (1999) *J. Bacteriol.*, 181, 1256-1263), and other genes from a variety of organisms. In addition, the HMG1 gene from *Saccharomyces cerevisiae* has a function of imparting a prenylalcohol production capacity to yeast as a result of promotion of the expression thereof in yeast, which is disclosed in, for example, JP Patent No. 3894119, JP Patent No. 3838033, and JP Patent No. 3918185. In the present invention, the HMG1 genes disclosed in JP Patent No. 3894119, JP Patent No. 3838033, and JP Patent No. 3918185 and the mutant HMG1 gene can be used.

In addition, the recombinant yeast of the present invention can cause high expression of the HMG-CoA reductase gene by incorporating the above HMG-CoA reductase gene into a vector so as to result in high expression of the gene and introducing the obtained expression vector into a host yeast described below. Alternatively, high expression of the HMG-CoA reductase gene may be caused by modifying the promoter region of the HMG-CoA reductase gene that is endogenously present in a host yeast described below.

Host Yeast

In the present invention, a host yeast into which the aforementioned HMG-CoA reductase gene, the ADP-ribose pyrophosphatase gene, and/or the yhfR gene are(is) introduced is not particularly limited. Examples thereof include ascomycetous yeast of *Ascomycetes*, basidiomycetous yeast of *Basidiomycetes*, and deuteromycetouts yeast of *Deuteromycetes*. Examples of yeast that can be used include: ascomycetous yeast, and particularly budding yeast, such as *Saccharomyces cerevisiae* known as bakers' yeast, *Candida utilis*, or *Pichia pastris*; and fission yeast such as *Shizosaccharomyces pombe*. In addition, as a yeast, haploid yeast or diploid yeast known as so-called laboratory yeast may be used. Alternatively, a multiploid yeast having the chromosome structure of a diploid or greater polyploid yeast known as so-called practical yeast may be used. In the case of *S. cerevisiae*, examples of yeasts that can be used include the A451 strain, the EUG8 strain, the EUG12 strain, the EUG27 strain, the YPH499 strain, the YPH500 strain, the W303-1A strain, the W303-1B strain, and the AURGG101 strain.

Also, it is possible to use yeast in which the expression of the HMG-CoA reductase gene has been strengthened disclosed in JP Patent No. 3894119, JP Patent No. 3838033, and JP Patent No. 3918185 described above. Specifically, the recombinant yeast of the present invention may be produced by introducing the ADP-ribose pyrophosphatase gene and/or the yhfR gene into yeast in which the expression of the HMG-CoA reductase gene has been strengthened. Here, the phrase "the expression of the HMG-CoA reductase gene has been strengthened" means that the expression level (i.e. "amount") of the HMG-CoA reductase gene is significantly improved. Here, the term "significantly" refers to a situation in which the expression amount of the HMG-CoA reductase gene is increased to a statistically significant extent compared with that of yeast not being strengthened the expression of the gene, e.g. wild-type yeast.

Transformation of Host Yeast

Any conventionally known technique may be used for introducing the above HMG-CoA reductase gene, the ADP-ribose pyrophosphatase gene, and/or the yhfR gene into the aforementioned host yeast. For example, when each such gene is introduced, plasmid DNA, bacteriophage, retrotransposon DNA, yeast artificial chromosome DNA (YAC: yeast artificial chromosome), and the like, which can be genetically retained in a host yeast, are constructed. Examples of plasmid DNA include: YCp-type Escherichia coli-yeast shuttle vectors such as pRS413, pRS414, pRS415, pRS416, YCp50, pAUR112, and pAUR123; YEp-type Escherichia coli-yeast shuttle vectors such as pYES2 and YEp13; YIp-type Escherichia coli-yeast shuttle vectors such as pRS403, pRS404, pRS405, pRS406, pAUR101, and pAUR135; Escherichia coli-derived plasmids (e.g.: ColE plasmids such as pBR322, pBR325, pUC18, pUC19, pUC118, pUC119, pTV118N, pTV119N, pBluescript, pHSG298, pHSG396, and pTrc99A; p15A plasmids such as pACYC177 and pACYC184; and pSC101 plasmids such as pMW118, pMW119, pMW218, and pMW219); and Bacillus subtilis-derived plasmids (e.g., pUB110 and pTP5). Examples of phage DNA include λ phages (Charon4A, Charon21A, EMBL3, EMBL4, λgt10, λgt11, and XZAP), φX174, M13mp18, and M13mp19. Examples of retrotransposons include a Ty factor. Examples of YAC vectors include pYACC2.

In addition, as a transcription promoter that causes the HMG-CoA reductase gene, the ADP-ribose pyrophosphatase gene, and the yhfR gene to be expressed in a host cell, any promoter for stable expression or promoter for inducible expression may be used. A promoter for stable expression is, for example, a transcription promoter for a gene involved in a major metabolic pathway, such promoter having transcription activity regardless of growth conditions and the like. A promoter for inducible expression is a promoter that induces transcription under specific growth conditions.

Any transcription promoter may be used as long as it exhibits activity in the aforementioned host yeast. For example, a GAL1 promoter, a GAL10 promoter, a TDH3 (GAP) promoter, an ADH1 promoter, a TEF2 promoter, and the like can be used for expression in yeast. Further, if desired, cis elements such as enhancers, splicing signals, polyA addition signals, selection markers, and the like can be ligated to such promoters. In addition, examples of selection markers include: marker genes with non-auxotrophic phenotypes such as URA3, LEU2, TRP1, HIS5, ADE2, and LYS2; and antibiotic-resistant genes such as Ampr, Tetr, Cmr, Kmr, AUR1-C, can1, Bla, Shble, and Neo.

As a transcription terminator, a terminator from any gene may be used as long as it exhibits activity in the aforementioned host yeast. Examples of terminators for expression in yeast include the ADH1 terminator and the CYC1 terminator.

Meanwhile, any conventional method known as a yeast transformation method can be applied as a method for introducing a plasmid incorporating the HMG-CoA reductase gene, the ADP-ribose pyrophosphatase gene, and the yhfR gene into a host yeast. Specific examples of such method that can be carried out include, but are not limited to, an electroporation method described in "Meth. Enzym., 194, p 182 (1990)," a spheroplast method described in "Proc. Natl. Acad. Sci. USA, 75 p. 1929 (1978)," a lithium acetate method described in "J. Bacteriology, 153, p. 163 (1983)," and methods described in "Proc. Natl. Acad. Sci. USA, 75 p. 1929 (1978)" and "Methods in yeast genetics, 2000 Edition: A Cold Spring Harbor Laboratory Course Manual."

It is possible to confirm whether or not a gene has been introduced into a host yeast by the PCR (polymerase chain reaction) method, the Southern hybridization method, or the like. For instance, PCR may be carried out by preparing DNA from a recombinant yeast and designing a primer specific to an introduced gene. Thereafter, PCR amplification products are subjected to agarose gel electrophoresis, polyacrylamide gel electrophoresis, capillary electrophoresis, or the like. Then, staining with ethidium bromide, an SYBR Green solution, or the like or DNA detection with a UV detector is carried out such that amplification products can be detected with peaks, thereby confirming introduced DNA. Alternatively, PCR is carried out using primers that have been preliminarily labeled with a fluorescent dye or the like so as to detect amplification products.

Branched Alcohol Production

The recombinant yeast of the present invention produced as above can produce saturated branched alcohols such as 2-methyl-1-butanol and 3-methyl-1-butanol in a medium when cultured in an ordinary medium. WO 2007/139925 reports that Escherichia coli into which the nudF gene or the yhfR gene of Bacillus subtilis have been introduced can synthesize unsaturated branched alcohols such as 3-methyl-2-butene-1-ol and 3-methyl-3-butene-1-ol. When compared with the above, it can be said that the recombinant yeast of the present invention has an unpredictable effect of producing saturated branched alcohols such as 2-methyl-1-butanol and 3-methyl-1-butanol.

In addition, saturated branched alcohols such as 2-methyl-1-butanol and 3-methyl-1-butanol produced in a medium can be isolated/produced by a known method such as distillation. When unsaturated branched alcohols are isolated/purified by a distillation method, a polymerization reaction via unsaturated bonds in a molecular chain or a chemical reaction with other components takes place in some cases, which might result in reduction of branched alcohol productivity. In addition, since unsaturated branched alcohols have lower acid stability than saturated branched alcohols, it is necessary to reduce unsaturated bonds for conversion into saturated branched alcohols. Meanwhile, even if saturated branched alcohols produced by the recombinant yeast of the present invention are isolated/purified by a distillation method, it is possible to avoid loss due to the above polymerization reaction or chemical reaction. Therefore, when branched alcohols are produced with the use of the recombinant yeast of the present invention, excellent productivity can be achieved. When branched alcohol is produced with the use of the recombinant yeast of the present invention, low-cost production can be achieved. This is because a step of reducing unsaturated bonds can be omitted.

EXAMPLES

The present invention is hereafter described in greater detail with reference to the following examples, although the technical scope of the present invention is not limited thereto.

Example 1

Production of the HMG1/YPH499 Strain

In this Example, Saccharomyces cerevisiae capable of causing high expression of the HMG-CoA reductase gene was produced first. Specifically, the HMG-CoA reductase gene derived from the Saccharomyces cerevisiae DBY746 strain was introduced into the Saccharomyces cerevisiae YPH499 strain. A detailed explanation is as follows.

(1) Preparation of pRS404Tcyc and pRS406Tcyc

A CYC1 transcription terminator CYC1t fragment was prepared by PCR with the use of a pair of primers designed as shown below.

XhoI-Tcyc1FW:
(SEQ ID NO: 5)
5' TGC ATC TCG AGG GCC GCA TCA TGT AAT TAG 3'

ApaI-Tcyc1RV:
(SEQ ID NO: 6)
5' CAT TAG GGC CCG GCC GCA AAT TAA AGC TTC CG 3'

In addition, pYES2 (Invitrogen) (0.1 mg) as a PCR template and the above pair of primers (50 pmol each) were used. The PCR reaction solution was a solution (50 ml) containing 1× pfu buffer with MgSO$_4$ (Promega), 10 nmol dNTP, a Pfu DNA polymerase (Promega) (1.5 u), and a perfect match polymerase enhancer (Stratagene) (1 ml). PCR thermal cycles were as follows: 95° C. for 2 minutes; 30 cycles of 95° C. for 45 seconds, 60° C. for 30 seconds, and 72° C. for 1 minute; and 72° C. for 5 minutes. The resulting solution was stored as a stock solution at 4° C.

Thereafter, DNA amplified by PCR was cleaved with XhoI and ApaI, followed by purification of a 260-bp DNA fragment by agarose gel electrophoresis. Then, pRS404 and pRS406 (Stratagene) were separately prepared and a purified DNA fragment was inserted into the XhoI-ApaI site of each thereof. The obtained plasmids were referred to as pRS404Tcyc and pRS406Tcyc, respectively.

(2) Production of a TDH3p Fragment

A DNA fragment containing a TDH3p (GAP) promoter was prepared by PCR with the use of genomic DNA of the *Saccharomyces cerevisiae* YPH499 strain (Stratagene) as a template and a pair of primers designed as shown below. In addition, for the genomic DNA, a "GenTLE Kun" yeast genomic DNA preparation kit (TAKARA Bio Inc.) was used.

SacI-Ptdh3FW:
(SEQ ID NO: 7)
5' CAC GGA GCT CCA GTT CGA GTT TAT CAT TAT CAA 3'

SacII-Ptdh3RV:
(SEQ ID NO: 8)
5' CTC TCC GCG GTT TGT TTG TTT ATG TGT GTT TAT TC 3'

For PCR, genomic DNA (0.46 mg) as a template and the above pair of primers (100 pmol each) were used. In addition, the reaction solution used for PCR was a solution (100 ml) containing 1×ExTaq buffer (TAKARA Bio Inc.), dNTP (20 nmol), ExTaq DNA polymerase (TAKARA Bio Inc.) (0.5 u), and a perfect match polymerase enhancer (1 ml). PCR thermal cycles were as follows: 95° C. for 2 minutes; 30 cycles of 95° C. for 45 seconds, 60° C. for 1 minute, and 72° C. for 2 minutes; and 72° C. for 4 minutes. The resulting solution was stored as a stock solution at 4° C.

Thereafter, DNA amplified by PCR was cleaved with SacI and SacII. Then, a 680-bp DNA fragment was purified by agarose gel electrophoresis. The obtained DNA fragment was designated as TDH3p.

(3) Production of a 2 μmOriSN Fragment pYES2 (Invitrogen) was cleaved with SspI and NheI. A 1.5-kbp fragment containing a 2 μm DNA replication origin (2 μm ori) was purified by agarose gel electrophoresis and blunt-ended with a Klenow enzyme. The obtained DNA fragment was designated as 2 μmOriSN.

(4) Production of pRS434GAP and pRS436GAP

2 μmOriSN was inserted into the BAP (bacterial alkaline phosphatase, TAKARA Bio Inc.)-treated NaeI site of each of pRS404Tcyc and pRS406Tcyc obtained in (1) above. The reaction product was transformed into an *E. coli* SURE2 strain according to a general method. Transformed *Escherichia coli* was cultured according to a general method for preparation of plasmid DNA. The obtained plasmid DNA was cleaved with DraIII and EcoRI or with PstI and PvuII, followed by agarose gel electrophoresis. Then, the insertion of 2 μm on and the direction of insertion were checked. Plasmids obtained by separately inserting 2 μm on into pRS404Tcyc and pRS406Tcyc obtained in (1) above in the same direction with pYES2 were designated as pRS434Tcyc2 μmOri and pRS436Tcyc2 μmOri, respectively.

Then, TDH3p (a DNA fragment containing a transcription promoter) obtained in (2) above was inserted into the SacI-SacII site of each of pRS434Tcyc2 μmOri and pRS436Tcyc2 μmOri. The finally obtained plasmids were designated as pRS434GAP and pRS436GAP, respectively.

(5) Production of pRS504

A pRS504 vector was produced by introducing the *Sacharomyces cerevisiae* rDNA sequence into pRS434GAP produced in (4) above. For the rDNA sequence, Nieto A et al. (1999) *Biotechnol. Prog.*, 15 (3), 459-66 was used as a reference. A PCR reaction was carried out as in the above case with the use of primers shown below.

AatTRP1-50F:
(SEQ ID NO: 9)
5'-TTT CCG ACG TCC ACG TGA GTA TAC GTG ATT AAG-3'

TRP1d-R:
(SEQ ID NO: 10)
5'-AGG CAA GTG CAC AAA CAA TAC TT-3'

Specifically, first, PCR was carried out with the use of pRS434GAP produced in (4) above as a template DNA, AatTRP1-50F, and TRP1d-R for amplification of a 0.8-kb TRP1d fragment. Then, PCR was carried out with the use of phosphorylated primers shown below and genomic DNA of the *Saccharomyces cerevisiae* YPH499 (ATCC 204679) strain for amplification of a portion of rDNA; namely, a 1.3-kb fragment (R47).

R4:
(SEQ ID NO: 11)
5'-ATG AGA GTA GCA AAC GTA AGT CTA A-3'

K-R7:
(SEQ ID NO: 12)
5'-TGA CTG GTA CCT TTC CTC TAA TCA GGT TCC ACC-3'

Next, the TRP1d and R47 fragments were purified by agarose gel electrophoresis, followed by ligation. PCR was carried out using the resulting reaction solution as a template and AatTRP1-50F and K-R7 primers for amplification of a 2.0-kb fragment (TR47) comprising TRP1d and R47 ligated to each other. TR47 was further purified by agarose gel electrophoresis, followed by subcloning into a pCR-Blunt II TOPO vector (Invitrogen). The obtained vector was designated as TOPO-TR47. As a result of sequencing of the TR47 fragment, it was confirmed that no mutation was contained therein. Subsequently, TOPO-TR47 and pRS434GAP were digested with restriction enzymes Aat11 and Kpn1 such that a 3.2-kb fragment comprising a TR47 fragment and a TDH3 promoter was excised therefrom, followed by ligation. The obtained plasmid was referred to as pRS504.

(6) Production of a pDI626 Vector

Inverse PCR was carried out using pRS436GAP produced in (4) above as template DNA and a pair of primers that had been phosphorylated with T4 polynucleotide kinase for amplification of a 4.7-kb fragment.

```
T7-F:
                                        (SEQ ID NO: 13)
5'-GCG TAA TAC GAC TCA CTA TAG GG-3'

2um-R:
                                        (SEQ ID NO: 14)
5'-CCT GAT GCG GTA TTT TCT CCT TAC-3'
```

The obtained fragment was subjected to self-ligation, followed by degradation and removal of the template DNA with DpnI. Thus, a plasmid pRS436-2 μm comprising pRS436GAP from which 2 μm Ori had been removed was produced.

Next, PCR was carried out with the use of Aat-TY1F and Sse-TY2R primers shown below and genomic DNA of the *Saccharomyces cerevisiae* YPH499 (ATCC 204679) strain. The amplified fragment was designated as T12.

```
Aat-TY1F:
                                        (SEQ ID NO: 15)
5'-GAC GTC TGT TGG AAT AAA AAT CCA CTA TCG-3'

Sse-TY2R:
                                        (SEQ ID NO: 16)
5'-CCT GCA GGA TTC CGT TTT ATA TGT TTA TAT

TCA TTG-3'
```

Similarly, PCR was carried out using primers shown below and genomic DNA of the *Saccharomyces cerevisiae* YPH499 (ATCC 204679) strain. The amplified fragment was designated as T34.

```
SAC 1-TY3F:
                                        (SEQ ID NO: 17)
5'-GAG CTC GAG GAA TAA TCG TAA TAT TAG TAT

GTA-3'

Sse-TY4R:
                                        (SEQ ID NO: 18)
5'-GCG CGC TGA GAA ATT TGT GGG TAA TTA GAT

AAT-3'
```

Each of the amplified T12 and T34 fragments was a portion of the LTR sequence of YOLWTy1-1 (chromosome XV; from coordinates 117,702 to 123,627). The amplified T12 and T34 fragments were separately subcloned into a pCR-Blunt II TOPO vector. The obtained vectors were designated as TOPO-T12 and TOPO-T34, respectively. The vectors were subjected to sequencing, and thus no PCR error was confirmed therein. TOPO-T12 was digested with AatII and Sse8387I. A T12 fragment was excised therefrom, followed by ligation into the AatII-Sse8387I site of pRS436-2 μm. Thus, a plasmid pDIT12 was produced. Similarly, TOPO-T34 was digested with the use of SacI and BssHII. A T34 fragment was excised therefrom, followed by ligation into the SacI-BssHII site of pDIT12. Thus, a plasmid pDI626 was produced.

(7) Cloning of the "HMG1" HMG-CoA Reductase Gene

PCR was carried out using a "Quick-Clone cDNA" cDNA library from *Saccharomyces cerevisiae* DBY746 (Clonetech) as a template and the pair of primers shown below.

```
Primer 1:
                                        (SEQ ID NO: 19)
5'-ATG CCG CCG CTA TTC AAG GGA CT-3'

Primer 2:
                                        (SEQ ID NO: 20)
5'-TTA GGA TTT AAT GCA GGT GAC GG-3'
```

In addition, the PCR reaction solution was a solution (50 μl) containing Perfect Match (Stratagene) (1 μl), a 10× ExTaq buffer (TAKARA Bio Inc.) (5 μl), a 2.5 mM dNTP mix (4 μl), 5 U/μl ExTaq (TAKARA Bio Inc.) (1 μl), and Primers 1 and 2 (10 pmol each). PCR thermal cycles were as follows: 30 cycles of 94° C. for 45 seconds, 55° C. for 1 minute, and 72° C. for 2 minutes.

The amplified fragment (approximately 3.2 kb) was subjected to T/A cloning into a pT7Blue-T vector for determination of the nucleotide sequence of the HMG1 region. As a result of comparison, the sequence was found to be different from the HMG1 gene sequence from *Saccharomyces cerevisiae* registered with GenBank (http://www.neb.nih.gov/Genbank/index.html) at 12 sites. Of these, 3 sites were confirmed to have a mutation that could influence the amino acid sequence (S68F, L607S, and H909R). The produced plasmid DNA was designated as pT7HMG1.

Next, in order to correct PCR errors, pT7HMG1 was cleaved with SmaI, ApaL1, and SalI and then a 3.2-kbp fragment was prepared by agarose electrophoresis. The fragment was inserted into the SmaI-SalI site of a pALTER-1 (Promega) vector such that pALHMG1 was produced. After alkaline denaturation, pALHMG1 was subjected to annealing with mutated oligos (Oligos 1 to 3) shown below, an Amp repair oligo (Promega), and a Tet knockout oligo (Promega). The resultant was introduced into the *Escherichia coli* ES1301 strain (Promega). Subsequently, a transformant retaining a site-specifically mutated plasmid was subjected to enrichment culture with 125 μg/ml ampicillin such that plasmid DNA was prepared.

```
Oligo 1:
                                        (SEQ ID NO: 21)
5'-CCA AAT AAA GAC TCC AAC ACT CTA TTT-3'

Oligo 2:
                                        (SEQ ID NO: 22)
5'-GAA TTA GAA GCA TTA TTA AGT AGT GGA-3'

Oligo 3:
                                        (SEQ ID NO: 23)
5'-GGA TTT AAC GCA CAT GCA GCT AAT TTA-3'
```

As a result of analysis of the nucleotide sequence of the prepared plasmid DNA, the aforementioned mutations at 3 sites were confirmed to have been corrected. The plasmid was designated as pALHMG106.

(8) Production of pRS504HMG1 pALHMG106 produced in (7) above was cleaved with SmaI and SalI. Then, a 3.2-kb HMG1 gene fragment was purified by agarose electrophoresis. The fragment was inserted into the SmaI-SalI site of pRS434GAP produced in (4) above such that pRS434GAP-HMG1 was obtained. Next, PCR was carried out with the use of pRS434GAP-HMG1 as a template and primers shown below for amplification of a fragment between the initiation codon and the Tth111I site (647 bp reckoned from the ATG initiation codon) of the HMG1 gene.

SacHMG1-F:
(SEQ ID NO: 24)
5'-CCG CGG AAC AAA ATG CCG CCG CTA TTC AAG GG-3'

TthHMG647R:
(SEQ ID NO: 25)
5'-GAC CCG GTC TTC CTC ATG TC-3'

With the use of the SacHMG1-F primer, the AACAAA sequence and the SacII site were added upstream of the HMG1 initiation codon. The PCR product was subcloned into a pMCR2.1-TOPO vector (Invitrogen) and it was confirmed to have no PCR error by sequencing. A SacII-Tth111I fragment was excised from the obtained vector so as to be replaced by a SacII-Tth111I fragment of pRS434GAP-HMG1. The obtained plasmid was designated as pRS434GAPa-HMG1. pRS434GAPa-HMG1 was digested with SacII and XhoI. A 3.2-kb HMG1 fragment was excised therefrom, followed by ligation into the SacII-XhoI site of pRS504 produced in (5) above. The obtained plasmid was designated as pRS504HMG1.

(9) Production of the HMG1/YPH499 Strain pRS504HMG1 (20 μg) produced in (8) above was cleaved with BstPI for linearization. Linearized pRS504HMG1 was recovered by ethanol precipitation and dissolved in sterile water (5 μl). pRS504HMG1 was introduced into *Saccharomyces cerevisiae* YPH499 (Stratagene) with the use of a Frozen EZ yeast transformation kit (Zymoresearch). A strain grown in a tryptophan-free YNB yeast minimal medium (Difco) was subjected to colony PCR such that the HMG1 gene was confirmed to have been introduced therein. The obtained strain was designated as HMG1/YPH499.

(10) Production of the NUDF/YPH499 Strain and the YHFR/YPH499 Strain

Figure 1:
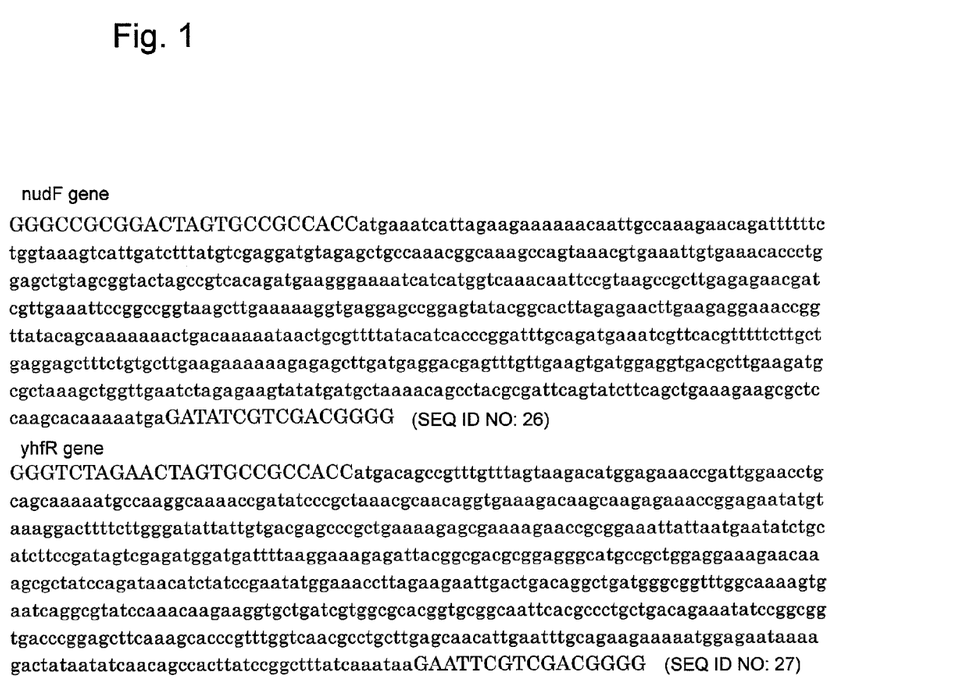
FIG. 1 shows the nucleotide sequence of a DNA fragment optimized to serve as a codon for *Saccharomyces cerevisiae* based on the nucleotide sequences of the nudF gene and the yhfR gene from *Bacillus subtilis* registered with GenBank.

A DNA fragment (FIG. 1) optimized for a codon of *Saccharomyces cerevisiae* based on the nucleotide sequences of the nudF gene and the yhfR gene from *Bacillus subtilis* registered with GenBank (http://www.neb.nih.gov/Genbank/index.html) was synthesized (Operon Biotechnologies).

In addition, GGGCCGCGGACTAGTGCCGCCACC and GGGTCTAGAACTAGTGCCGCCACC were added to the non-translation region upstream of ORF of the nudF gene and that of the yhfR gene, respectively. Further, GATATCGTC-GACGGGG and GAATTCGTCGACGGGG were added to the non-translation region downstream of ORF of the nudF gene and that of the yhfR gene, respectively (capital letters in FIG. 1).

A DNA fragment of the nudF gene represented by SEQ ID NO: 26 was digested with SpeI and SalI and inserted into the SpeI-SalI site of the pDI626 produced in (6) above. The obtained plasmid was designated as PDI626NUDF. In addition, a DNA fragment of the yhfR gene represented by SEQ ID NO: 27 was digested with SpeI and SalI and inserted into the SpeI-SalI site of pDI626 produced in (6) above. The obtained plasmid was designated as PDI626YHFR.

Each of PDI626NUDF and PDI626YHFR (22 μg each) obtained above was cleaved with AatII and BssHII for linearization. Linearized PDI626NUDF and PDI626YHFR were separately recovered by ethanol precipitation and dissolved in sterile water (5 μl). With the use of a Frozen EZ yeast transformation kit (Zymoresearch), PDI626NUDF and PDI626YHFR were separately introduced into *Saccharomyces cerevisiae* YPH499 (Stratagene). A strain grown in a uracil-free yeast minimal medium (BIO101) was collected as a strain having the nudF gene or yhfR gene introduced therein. PCR was carried out in order to confirm the occurrence of gene introduction. The obtained strains were designated as the NUDF/YPH499 strain and the YHFR/YPH499 strain, respectively.

(11) Production of the NUDF/HMG1/YPH499 Strain and the YHFR/HMG1/YPH499 Strain

PDI626NUDF and PDI626YHFR (22 μg each) obtained in (10) above were cleaved with AatII and BssHII, respectively, for linearization. Linearized PDI626NUDF and PDI626YHFR were introduced into HMG1/YPH499 produced in (9) above in a similar manner. As a result of obtaining a uracil-independent strain, a transgenic strain was obtained. After confirmation of gene introduction by PCR, the obtained strains were designated as the NUDF/HMG1/YPH499 strain and the YHFR/HMG1/YPH499 strain, respectively.

(12) Branched Alcohol Synthesis Analysis

Culture Test

The NUDF/YPH499 strain and YHFR/YPH499 strain produced in (10) above and the NUDF/HMG1/YPH499 strain, the YHFR/HMG1/YPH499 strain, and the *Saccharomyces cerevisiae* YPH499 strain produced in (11) above were precultured in an SD medium (-Trp, -Ura) at 30° C. Next, a 2-ml SD medium (-Trp, -Ura) contained in a sterile disposable glass test tube (IWAKI) was inoculated separately with each preculture solution (1%). Each tube was covered with an aluminium cap and subjected to shake culture at 30° C. under aerobic conditions.

Extraction and Analysis

Ethyl acetate (2 ml) and methanol (0.3 ml) were added to each test tube cryopreserved at −30° C. after the above culture, followed by agitation with a vortex mixer. Centrifugation was carried out with a centrifuge (Beckman Coulter, Inc.) (room temperature, 1200 rpm, 5 minutes) for separation of the solvent phase and the aqueous phase. Each solvent phase was transferred to a 2-ml vial bottle for a gas chromatograph mass spectrometer (GC/MS), to which a 1% undecanol solution (dissolved in ethanol) (10 μl) had been added as an internal standard. Each bottle was sealed with a Teflon-coated aluminium cap, followed by GC/MS analysis. At this time, 2-methyl-1-butanol serving as a standard solution was analyzed for quantification based on the TIC peak area ratio of the standard solution to undecanol used as the internal standard. GC/MS analysis was carried out with the use of an HP6890/5973 GC/MS system (Hewlett-Packard Development Company, L.P.) under the conditions listed in table 1.

TABLE 1

| <GC/MS analysis conditions> | |
|---|---|
| Inlet temperature: | 260° C. |
| Detector temperature: | 260° C. |
| Injection parameters | |
| Mode: | Automatic injection |
| Sample volume: | 2 μl |
| Instances of washing: | 3 times with methanol |
|  | Twice with chloroform |
| Split ratio: | 20:1 |
| Column: | Hewlett-Packard Development Company, L.P. HP-5MS (0.25 mm × 30 M; film thickness: 0.25 μm) |
| Carrier gas: | Helium: 1.0 ml/min |
| Oven temperature rise conditions: | Retention at 45° C. for 1 minute Temperature rise at 5° C./minute to 60° C. 100° C./minute to 320° C.; retention for 3.4 minutes |

Figure 2:
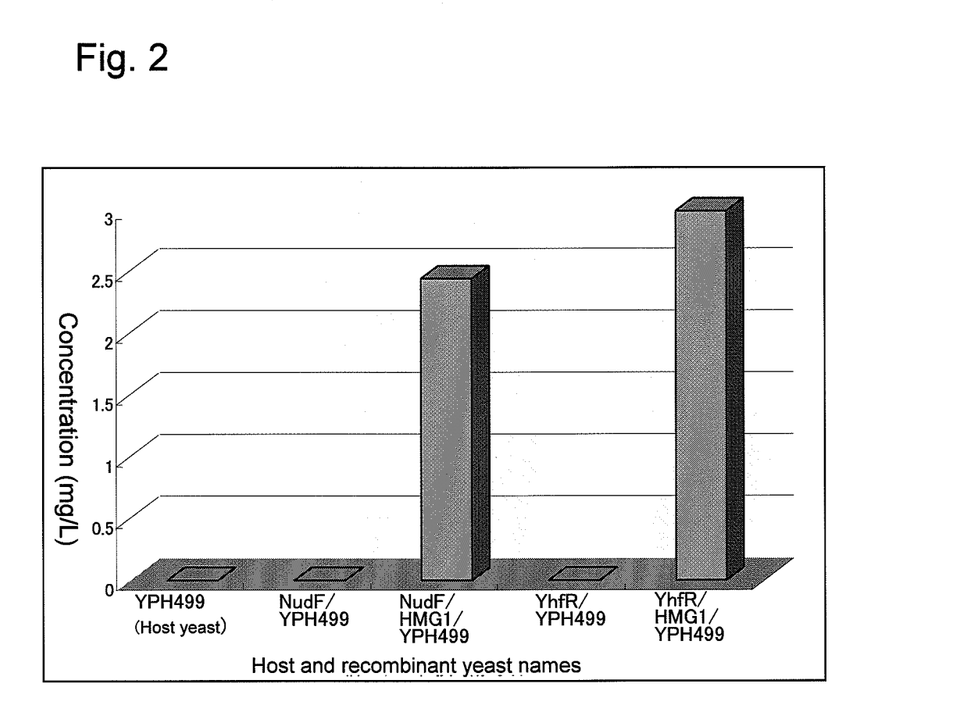
FIG. 2 is a characteristic chart showing results of GC/MS analysis of 2-methyl-1-butanol with the use of a host yeast and recombinant yeasts of the YPH499 strain.
Figure 3:
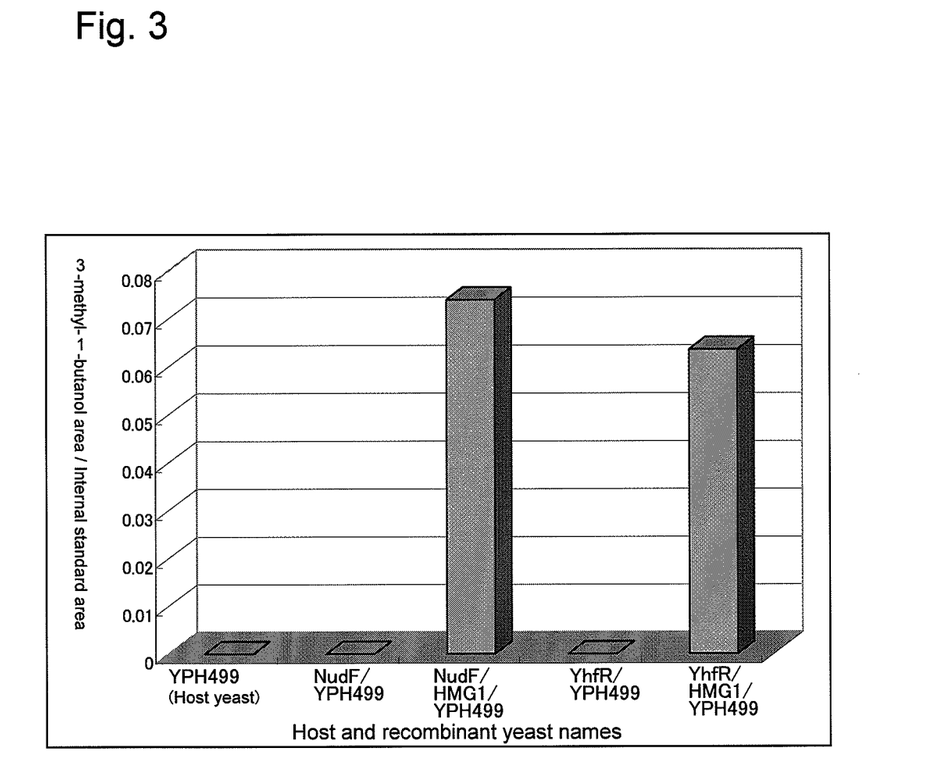
FIG. 3 is a characteristic chart showing results of GC/MS analysis of 3-methyl-1-butanol with the use of a host yeast and recombinant yeasts of the YPH499 strain.

FIG. 2 shows GC/MS analysis results. In addition, FIG. 3 shows results of comparison of the samples regarding the ratio of the 3-methyl-1-butanol area to the internal standard area, provided that the 3-methyl-1-butanol area was determined based on profiles obtained as GC/MS analysis results with the use of a database containing GC/MS mass spectrometry patterns. As shown in FIGS. 2 and 3, it has been revealed that 2-methyl-1-butanol and 3-methyl-1-butanol, which are saturated branched alcohols, can be produced with the use of a recombinant yeast that has been modified such that the expression level of the HMG-CoA gene and the expression levels of ADP-ribose pyrophosphatase gene and/or the yhfR gene become higher than those of a wild-type yeast.

The recombinant yeast of the present invention can produce 2-methyl-1-butanol and 3-methyl-1-butanol. Therefore, it can be used for production of automotive fuel and the like containing the butanols as components.

What is claimed is:

1. A method of production of saturated branched alcohol, comprising:

culturing in culture medium a recombinant yeast in which the HMG1 gene of *Saccharomyces cerevisiae* has been expressed to a high degree and the ADP-ribose pyrophosphatase gene and/or the yhfR gene are introduced so as to be expressed therein, wherein the ADP-ribose pyrophosphatase gene encodes a protein having the amino acid sequence of SEQ ID NO: 2 or a protein having an amino acid sequence with a 90% or more similarity to the amino acid sequence of SEQ ID NO: 2, and wherein the yhfR gene encodes a protein having the amino acid sequence of SEQ ID NO: 4 or a protein having an amino acid sequence with a 90% or more similarity to the amino acid sequence of SEQ ID NO: 4; and collecting the branched alcohol from the medium.

2. The method of production of saturated branched alcohol according to claim 1, wherein the ADP-ribose pyrophosphatase gene in the recombinant yeast is the nudF gene of *Bacillus subtilis*.

3. The method of production of saturated branched alcohol according to claim 1, wherein the yhfR gene in the recombinant yeast is the yhfR gene of *Bacillus subtilis*.

4. The method of production of saturated branched alcohol according to claim 1, wherein the recombinant yeast is a yeast having a mevalonic acid pathway.

5. The method of production of saturated branched alcohol according to claim 1, wherein the recombinant yeast is a yeast of the genus *Saccharomyces*.

6. The method of production of saturated branched alcohol according to claim 5, wherein the recombinant yeast is *Saccharomyces cerevisiae*.

7. The method of production of saturated branched alcohol according to claim 1, wherein 2-methyl-1-butanol and 3-methyl-1-butanol is collected as the branched alcohol.

* * * * *

SEQUENCE LISTING

<160> NUMBER OF SEQ ID NOS: 27

<210> SEQ ID NO 1
<211> LENGTH: 555
<212> TYPE: DNA
<213> ORGANISM: Bacillus subtilis
<220> FEATURE:
<221> NAME/KEY: CDS
<222> LOCATION: (1)..(555)

<400> SEQUENCE: 1

```
atg aaa tca tta gaa gaa aaa aca att gcc aaa gaa cag att ttt tcg      48
Met Lys Ser Leu Glu Glu Lys Thr Ile Ala Lys Glu Gln Ile Phe Ser
1               5                   10                  15 ggt aaa gtc att gat ctt tat gtc gag gat gta gag ctg cca aac ggc      96
Gly Lys Val Ile Asp Leu Tyr Val Glu Asp Val Glu Leu Pro Asn Gly
            20                  25                  30 aaa gcc agt aaa cgt gaa att gtg aaa cac cct gga gct gta gcg gta     144
Lys Ala Ser Lys Arg Glu Ile Val Lys His Pro Gly Ala Val Ala Val
        35                  40                  45 cta gcc gtc aca gat gaa ggg aaa atc atc atg gtc aaa caa ttc cgt     192
Leu Ala Val Thr Asp Glu Gly Lys Ile Ile Met Val Lys Gln Phe Arg
    50                  55                  60 aag ccg ctt gag cgg acg atc gtt gaa att ccg gcc ggt aag ctt gaa     240
Lys Pro Leu Glu Arg Thr Ile Val Glu Ile Pro Ala Gly Lys Leu Glu
65                  70                  75                  80 aaa ggt gag gag ccg gag tat acg gca ctt cgg gaa ctt gaa gag gaa     288
Lys Gly Glu Glu Pro Glu Tyr Thr Ala Leu Arg Glu Leu Glu Glu Glu
                85                  90                  95 acc ggt tat aca gca aaa aaa ctg aca aaa ata act gcg ttt tat aca     336
Thr Gly Tyr Thr Ala Lys Lys Leu Thr Lys Ile Thr Ala Phe Tyr Thr
            100                 105                 110 tca ccc gga ttt gca gat gaa atc gtt cac gtt ttt ctt gct gag gag     384
Ser Pro Gly Phe Ala Asp Glu Ile Val His Val Phe Leu Ala Glu Glu
        115                 120                 125 ctt tct gtg ctt gaa gaa aaa cgg gag ctt gat gag gac gag ttt gtt     432
Leu Ser Val Leu Glu Glu Lys Arg Glu Leu Asp Glu Asp Glu Phe Val
    130                 135                 140 gaa gtg atg gag gtg acg ctt gaa gat gcg cta aag ctg gtt gaa tcg     480
Glu Val Met Glu Val Thr Leu Glu Asp Ala Leu Lys Leu Val Glu Ser
145                 150                 155                 160 cgt gaa gta tat gat gct aaa aca gcc tac gcg att cag tat ctt cag     528
Arg Glu Val Tyr Asp Ala Lys Thr Ala Tyr Ala Ile Gln Tyr Leu Gln
                165                 170                 175 ctg aaa gaa gcg ctc caa gca caa aaa                                 555
Leu Lys Glu Ala Leu Gln Ala Gln Lys
            180                 185
```

<210> SEQ ID NO 2
<211> LENGTH: 185
<212> TYPE: PRT
<213> ORGANISM: Bacillus subtilis

```
<400> SEQUENCE: 2

Met Lys Ser Leu Glu Glu Lys Thr Ile Ala Lys Glu Gln Ile Phe Ser
1               5                   10                  15

Gly Lys Val Ile Asp Leu Tyr Val Glu Asp Val Glu Leu Pro Asn Gly
                20                  25                  30

Lys Ala Ser Lys Arg Glu Ile Val Lys His Pro Gly Ala Val Ala Val
            35                  40                  45

Leu Ala Val Thr Asp Glu Gly Lys Ile Ile Met Val Lys Gln Phe Arg
        50                  55                  60

Lys Pro Leu Glu Arg Thr Ile Val Glu Ile Pro Ala Gly Lys Leu Glu
65                  70                  75                  80

Lys Gly Glu Glu Pro Glu Tyr Thr Ala Leu Arg Glu Leu Glu Glu Glu
                85                  90                  95

Thr Gly Tyr Thr Ala Lys Lys Leu Thr Lys Ile Thr Ala Phe Tyr Thr
            100                 105                 110

Ser Pro Gly Phe Ala Asp Glu Ile Val His Val Phe Leu Ala Glu Glu
        115                 120                 125

Leu Ser Val Leu Glu Glu Lys Arg Glu Leu Asp Glu Asp Glu Phe Val
    130                 135                 140

Glu Val Met Glu Val Thr Leu Glu Asp Ala Leu Lys Leu Val Glu Ser
145                 150                 155                 160

Arg Glu Val Tyr Asp Ala Lys Thr Ala Tyr Ala Ile Gln Tyr Leu Gln
                165                 170                 175

Leu Lys Glu Ala Leu Gln Ala Gln Lys
            180                 185

<210> SEQ ID NO 3
<211> LENGTH: 579
<212> TYPE: DNA
<213> ORGANISM: Bacillus subtilis
<220> FEATURE:
<221> NAME/KEY: CDS
<222> LOCATION: (1)..(579)

<400> SEQUENCE: 3 atg aca gcc gtt tgt tta gta aga cat gga gaa acc gat tgg aac ctg        48
Met Thr Ala Val Cys Leu Val Arg His Gly Glu Thr Asp Trp Asn Leu
1               5                   10                  15 cag caa aaa tgc caa ggc aaa acc gat atc ccg cta aac gca aca ggt        96
Gln Gln Lys Cys Gln Gly Lys Thr Asp Ile Pro Leu Asn Ala Thr Gly
                20                  25                  30 gaa cgc caa gca aga gaa acc gga gaa tat gta aag gac ttt tct tgg       144
Glu Arg Gln Ala Arg Glu Thr Gly Glu Tyr Val Lys Asp Phe Ser Trp
            35                  40                  45 gat att att gtg acg agc ccg ctg aaa aga gcg aaa aga acc gcg gaa       192
Asp Ile Ile Val Thr Ser Pro Leu Lys Arg Ala Lys Arg Thr Ala Glu
        50                  55                  60 att att aat gaa tat ctg cat ctt ccg ata gtc gag atg gat gat ttt       240
Ile Ile Asn Glu Tyr Leu His Leu Pro Ile Val Glu Met Asp Asp Phe
65                  70                  75                  80 aag gaa cgc gat tac ggc gac gcg gag ggc atg ccg ctg gag gaa cgg       288
Lys Glu Arg Asp Tyr Gly Asp Ala Glu Gly Met Pro Leu Glu Glu Arg
                85                  90                  95 aca aag cgc tat cca gat aac atc tat ccg aat atg gaa acc tta gaa       336
Thr Lys Arg Tyr Pro Asp Asn Ile Tyr Pro Asn Met Glu Thr Leu Glu
            100                 105                 110 gaa ctc act gac agg ctg atg ggc ggt ttg gca aaa gtg aat cag gcg       384
Glu Leu Thr Asp Arg Leu Met Gly Gly Leu Ala Lys Val Asn Gln Ala
        115                 120                 125
```

```
tat cca aac aag aag gtg ctg atc gtg gcg cac ggt gcg gca att cac      432
Tyr Pro Asn Lys Lys Val Leu Ile Val Ala His Gly Ala Ala Ile His
        130                 135                 140 gcc ctg ctg aca gaa ata tcc ggt gac ccg gag ctt caa agc acc          480
Ala Leu Leu Thr Glu Ile Ser Gly Gly Asp Pro Glu Leu Gln Ser Thr
145                 150                 155                 160 cgt ctc gtc aac gcc tgc ctc agc aac att gaa ttt gca gaa gaa aaa      528
Arg Leu Val Asn Ala Cys Leu Ser Asn Ile Glu Phe Ala Glu Glu Lys
                165                 170                 175 tgg cgg ata aaa gac tat aat atc aac agc cac tta tcc ggc ttt atc      576
Trp Arg Ile Lys Asp Tyr Asn Ile Asn Ser His Leu Ser Gly Phe Ile
        180                 185                 190 aaa                                                                  579
Lys

<210> SEQ ID NO 4
<211> LENGTH: 193
<212> TYPE: PRT
<213> ORGANISM: Bacillus subtilis

<400> SEQUENCE: 4

Met Thr Ala Val Cys Leu Val Arg His Gly Glu Thr Asp Trp Asn Leu
1               5                   10                  15

Gln Gln Lys Cys Gln Gly Lys Thr Asp Ile Pro Leu Asn Ala Thr Gly
            20                  25                  30

Glu Arg Gln Ala Arg Glu Thr Gly Glu Tyr Val Lys Asp Phe Ser Trp
        35                  40                  45

Asp Ile Ile Val Thr Ser Pro Leu Lys Arg Ala Lys Arg Thr Ala Glu
    50                  55                  60

Ile Ile Asn Glu Tyr Leu His Leu Pro Ile Val Glu Met Asp Asp Phe
65                  70                  75                  80

Lys Glu Arg Asp Tyr Gly Asp Ala Glu Gly Met Pro Leu Glu Glu Arg
                85                  90                  95

Thr Lys Arg Tyr Pro Asp Asn Ile Tyr Pro Asn Met Glu Thr Leu Glu
            100                 105                 110

Glu Leu Thr Asp Arg Leu Met Gly Gly Leu Ala Lys Val Asn Gln Ala
        115                 120                 125

Tyr Pro Asn Lys Lys Val Leu Ile Val Ala His Gly Ala Ala Ile His
    130                 135                 140

Ala Leu Leu Thr Glu Ile Ser Gly Gly Asp Pro Glu Leu Gln Ser Thr
145                 150                 155                 160

Arg Leu Val Asn Ala Cys Leu Ser Asn Ile Glu Phe Ala Glu Glu Lys
                165                 170                 175

Trp Arg Ile Lys Asp Tyr Asn Ile Asn Ser His Leu Ser Gly Phe Ile
            180                 185                 190

Lys

<210> SEQ ID NO 5
<211> LENGTH: 30
<212> TYPE: DNA
<213> ORGANISM: Artificial
<220> FEATURE:
<223> OTHER INFORMATION: Synthetic DNA

<400> SEQUENCE: 5
tgcatctcga gggccgcatc atgtaattag                                     30

<210> SEQ ID NO 6
```

```
<211> LENGTH: 32
<212> TYPE: DNA
<213> ORGANISM: Artificial
<220> FEATURE:
<223> OTHER INFORMATION: Synthetic DNA

<400> SEQUENCE: 6
cattagggcc cggccgcaaa ttaaagcctt cg                                    32

<210> SEQ ID NO 7
<211> LENGTH: 33
<212> TYPE: DNA
<213> ORGANISM: Artificial
<220> FEATURE:
<223> OTHER INFORMATION: Synthetic DNA

<400> SEQUENCE: 7
cacggagctc cagttcgagt ttatcattat caa                                   33

<210> SEQ ID NO 8
<211> LENGTH: 35
<212> TYPE: DNA
<213> ORGANISM: Artificial
<220> FEATURE:
<223> OTHER INFORMATION: Synthetic DNA

<400> SEQUENCE: 8
ctctccgcgg tttgtttgtt tatgtgtgtt tattc                                 35

<210> SEQ ID NO 9
<211> LENGTH: 33
<212> TYPE: DNA
<213> ORGANISM: Artificial
<220> FEATURE:
<223> OTHER INFORMATION: Synthetic DNA

<400> SEQUENCE: 9
tttccgacgt ccacgtgagt atacgtgatt aag                                   33

<210> SEQ ID NO 10
<211> LENGTH: 23
<212> TYPE: DNA
<213> ORGANISM: Artificial
<220> FEATURE:
<223> OTHER INFORMATION: Synthetic DNA

<400> SEQUENCE: 10
aggcaagtgc acaaacaata ctt                                              23

<210> SEQ ID NO 11
<211> LENGTH: 25
<212> TYPE: DNA
<213> ORGANISM: Artificial
<220> FEATURE:
<223> OTHER INFORMATION: Synthetic DNA

<400> SEQUENCE: 11
atgagagtag caaacgtaag tctaa                                            25

<210> SEQ ID NO 12
<211> LENGTH: 33
<212> TYPE: DNA
<213> ORGANISM: Artificial
<220> FEATURE:
<223> OTHER INFORMATION: Synthetic DNA

<400> SEQUENCE: 12
```

```
tgactggtac ctttcctcta atcaggttcc acc                             33
```

<210> SEQ ID NO 13
<211> LENGTH: 23
<212> TYPE: DNA
<213> ORGANISM: Artificial
<220> FEATURE:
<223> OTHER INFORMATION: Synthetic DNA

<400> SEQUENCE: 13

```
gcgtaatacg actcactata ggg                                        23
```

<210> SEQ ID NO 14
<211> LENGTH: 24
<212> TYPE: DNA
<213> ORGANISM: Artificial
<220> FEATURE:
<223> OTHER INFORMATION: Synthetic DNA

<400> SEQUENCE: 14

```
cctgatgcgg tattttctcc ttac                                       24
```

<210> SEQ ID NO 15
<211> LENGTH: 30
<212> TYPE: DNA
<213> ORGANISM: Artificial
<220> FEATURE:
<223> OTHER INFORMATION: Synthetic DNA

<400> SEQUENCE: 15

```
gacgtctgtt ggaataaaaa tccactatcg                                 30
```

<210> SEQ ID NO 16
<211> LENGTH: 36
<212> TYPE: DNA
<213> ORGANISM: Artificial
<220> FEATURE:
<223> OTHER INFORMATION: Synthetic DNA

<400> SEQUENCE: 16

```
cctgcaggat tccgttttat atgtttatat tcattg                          36
```

<210> SEQ ID NO 17
<211> LENGTH: 33
<212> TYPE: DNA
<213> ORGANISM: Artificial
<220> FEATURE:
<223> OTHER INFORMATION: Synthetic DNA

<400> SEQUENCE: 17

```
gagctcgagg aataatcgta atattagtat gta                             33
```

<210> SEQ ID NO 18
<211> LENGTH: 33
<212> TYPE: DNA
<213> ORGANISM: Artificial
<220> FEATURE:
<223> OTHER INFORMATION: Synthetic DNA

<400> SEQUENCE: 18

```
gcgcgctgag aaatttgtgg gtaattagat aat                             33
```

<210> SEQ ID NO 19
<211> LENGTH: 23
<212> TYPE: DNA
<213> ORGANISM: Artificial
<220> FEATURE:

<223> OTHER INFORMATION: Synthetic DNA

<400> SEQUENCE: 19
atgccgccgc tattcaaggg act                                    23

<210> SEQ ID NO 20
<211> LENGTH: 23
<212> TYPE: DNA
<213> ORGANISM: Artificial
<220> FEATURE:
<223> OTHER INFORMATION: Synthetic DNA

<400> SEQUENCE: 20
ttaggattta atgcaggtga cgg                                    23

<210> SEQ ID NO 21
<211> LENGTH: 27
<212> TYPE: DNA
<213> ORGANISM: Artificial
<220> FEATURE:
<223> OTHER INFORMATION: Synthetic DNA

<400> SEQUENCE: 21
ccaaataaag actccaacac tctattt                                27

<210> SEQ ID NO 22
<211> LENGTH: 27
<212> TYPE: DNA
<213> ORGANISM: Artificial
<220> FEATURE:
<223> OTHER INFORMATION: Synthetic DNA

<400> SEQUENCE: 22
gaattagaag cattattaag tagtgga                                27

<210> SEQ ID NO 23
<211> LENGTH: 27
<212> TYPE: DNA
<213> ORGANISM: Artificial
<220> FEATURE:
<223> OTHER INFORMATION: Synthetic DNA

<400> SEQUENCE: 23
ggatttaacg cacatgcagc taattta                                27

<210> SEQ ID NO 24
<211> LENGTH: 32
<212> TYPE: DNA
<213> ORGANISM: Artificial
<220> FEATURE:
<223> OTHER INFORMATION: Synthetic DNA

<400> SEQUENCE: 24
ccgcggaaca aaatgccgcc gctattcaag gg                          32

<210> SEQ ID NO 25
<211> LENGTH: 20
<212> TYPE: DNA
<213> ORGANISM: Artificial
<220> FEATURE:
<223> OTHER INFORMATION: Synthetic DNA

<400> SEQUENCE: 25
gacccggtct tcctcatgtc                                        20

<210> SEQ ID NO 26

```
<211> LENGTH: 598
<212> TYPE: DNA
<213> ORGANISM: Artificial
<220> FEATURE:
<223> OTHER INFORMATION: Synthetic DNA

<400> SEQUENCE: 26
gggccgcgga ctagtgccgc caccatgaaa tcattagaag aaaaaacaat tgccaaagaa      60
cagatttttt ctggtaaagt cattgatctt tatgtcgagg atgtagagct gccaaacggc     120
aaagccagta acgtgaaat tgtgaaacac cctggagctg tagcggtact agccgtcaca     180
gatgaaggga aaatcatcat ggtcaaacaa ttccgtaagc cgcttgagag aacgatcgtt     240
gaaattccgg ccggtaagct tgaaaaaggt gaggagccgg agtatacggc acttagagaa     300
cttgaagagg aaaccggtta tacagcaaaa aaactgacaa aaataactgc gttttataca     360
tcacccggat ttgcagatga aatcgttcac gttttcttg ctgaggagct ttctgtgctt     420
gaagaaaaaa gagagcttga tgaggacgag tttgttgaag tgatggaggt gacgcttgaa     480
gatgcgctaa agctggttga atctagagaa gtatatgatg ctaaaacagc ctacgcgatt     540
cagtatcttc agctgaaaga agcgctccaa gcacaaaaat gagatatcgt cgacgggg       598

<210> SEQ ID NO 27
<211> LENGTH: 622
<212> TYPE: DNA
<213> ORGANISM: Artificial
<220> FEATURE:
<223> OTHER INFORMATION: Synthetic DNA

<400> SEQUENCE: 27
gggtctagaa ctagtgccgc caccatgaca gccgtttgtt tagtaagaca tggagaaacc      60
gattggaacc tgcagcaaaa atgccaaggc aaaaccgata tcccgctaaa cgcaacaggt     120
gaaagacaag caagagaaac cggagaatat gtaaaggact tttcttggga tattattgtg     180
acgagcccgc tgaaaagagc gaaaagaacc gcggaaatta ttaatgaata tctgcatctt     240
ccgatagtcg agatggatga tttaaggaa agagattacg gcgacgcgga gggcatgccg     300
ctggaggaaa gaacaaagcg ctatccagat aacatctatc cgaatatgga aaccttagaa     360
gaattgactg acaggctgat gggcggtttg gcaaaagtga atcaggcgta tccaaacaag     420
aaggtgctga tcgtggcgca cggtgcggca attcacgccc tgctgacaga aatatccggc     480
ggtgacccgg agcttcaaag cacccgtttg gtcaacgcct gcttgagcaa cattgaattt     540
gcagaagaaa aatggagaat aaaagactat aatatcaaca gccacttatc cggctttatc     600
aaataagaat tcgtcgacgg gg                                              622
```